(12) United States Patent
Hoover et al.

(10) Patent No.: US 7,670,555 B2
(45) Date of Patent: Mar. 2, 2010

(54) PARALLEL GRIPPER FOR HANDLING MULTIWELL PLATE

(75) Inventors: Rex A. Hoover, TRITEK Corporation, 5263 Stewart Rd., Sumerduck, VA (US) 22742; Robert G. Hoover, Sumerduck, VA (US)

(73) Assignee: Rex A. Hoover, Sumerduck, VA (US)

( * ) Notice: Subject to any disclaimer, the term of this patent is extended or adjusted under 35 U.S.C. 154(b) by 567 days.

(21) Appl. No.: 11/517,339

(22) Filed: Sep. 8, 2006

(65) Prior Publication Data

US 2008/0063562 A1   Mar. 13, 2008

(51) Int. Cl.
  G01N 35/00   (2006.01)
  G01N 35/02   (2006.01)
  B25J 15/00   (2006.01)

(52) U.S. Cl. .............................. 422/65; 422/63; 422/64; 422/104; 436/43; 436/47; 436/48; 294/119.1; 901/36; 901/39; 414/729; 414/733; 414/744.8; 414/751.1

(58) Field of Classification Search .................. None
See application file for complete search history.

(56) References Cited

U.S. PATENT DOCUMENTS

| 4,579,380 | A | | 4/1986 | Zaremsky et al. |
|---|---|---|---|---|
| 4,699,414 | A | | 10/1987 | Jones |
| 4,808,898 | A | | 2/1989 | Pearson |
| 5,080,415 | A | * | 1/1992 | Bjornson ................. 294/119.1 |
| 5,122,342 | A | * | 6/1992 | McCulloch et al. .......... 422/65 |
| 5,609,381 | A | | 3/1997 | Thom et al. |
| 5,947,539 | A | * | 9/1999 | Long et al. ............... 294/119.1 |
| 6,496,309 | B1 | | 12/2002 | Bliton et al. |
| 6,932,557 | B2 | * | 8/2005 | Downs et al. ............... 414/741 |
| 2002/0114685 | A1 | * | 8/2002 | Inui ........................... 414/281 |
| 2003/0178866 | A1 | * | 9/2003 | Chae et al. ............... 294/119.1 |
| 2004/0256963 | A1 | | 12/2004 | Afflick et al. |
| 2005/0173446 | A1 | * | 8/2005 | Han et al. ..................... 221/15 |
| 2007/0059205 | A1 | * | 3/2007 | Ganz et al. ..................... 422/63 |
| 2007/0258858 | A1 | * | 11/2007 | Rasnow et al. ................ 422/63 |

* cited by examiner

Primary Examiner—P. Kathryn Wright
(74) Attorney, Agent, or Firm—Chandrakant Shroff (57) ABSTRACT

A parallel gripper for handling multiwell plates in an automated analysis system, moves individual multiwell plates between a plate storage array unit (i.e., plate hotel) and an imaging station. More particularly, the gripper has two parallel plate-gripping arms that move in equal, but opposite linear directions and are controlled using a stepper motor. Each of the arms has a shelf that provides support for the corresponding side edge of a multiwell plate.

1 Claim, 10 Drawing Sheets

PARALLEL GRIPPER FOR HANDLING MULTIWELL PLATE

BACKGROUND OF THE INVENTION

Multiwell analysis plates used in automated analytical equipment, including automated biological assay, are widely used. These plates are standardized for use in various instruments, such as epifluorescence multiwell imaging analysis, protein crystal detection and ELISA (Enzyme-Linked ImmunoSorbent Assay). Typically, plastic 96-well plates, having an 8×12 array of wells, are used; however, 6-, 384- and 1536-well plates, and other array arrangements are also used.

US Patent Application Publication No. 2004/0256963 filed by Afflick et al. published Dec. 23, 2004, is directed to an automated sample analysis system capable of handling a large number of multiwell plates. As shown in FIGS. 6-8 and discussed at paragraphs 51 and 89-99, this system uses a robotically operated plate handler. In particular, as stated at paragraph 93, the plate handler in this system does not grasp and lift the plates.

U.S. Pat. No. 6,496,309 issued to Bliton et al. on Dec. 17, 2002 discloses an automated CCD-based micro-array imaging system, but appears to be silent regarding any sample plate handler, e.g., handlers for the gene chip arrays.

U.S. Pat. No. 5,609,381 issued to Thom et al. on Mar. 11, 1997, U.S. Pat. No. 4,808,898 issued to Pearson on Feb. 28, 1989, U.S. Pat. No. 4,699,414 issued to Jones on Oct. 13, 1987, and U.S. Pat. No. 4,579,380 issued to Zaremsky et al. on Apr. 1, 1986, all exemplify parallel grippers that can be used with transporting robots. However, none of these teach or disclose the parallel gripper structure of the present invention using the stepper motor.

During gripping, the plastic plates can be unnecessarily squeezed by the prior gripping devices, causing the plates to buckle and adversely affecting the contents of the well. This can result in inaccurate analyses. Also, the prior gripping devices can grip the sides of the plates at uneven positions, which can adversely affect the analysis.

It is an object of the present invention to provide a parallel gripper usable with a multi-well plate handling robot to grip a multi-well plate that maintains the plate in a horizontal orientation, avoids disruptive squeezing of the plates during gripping, and minimizes or eliminates sudden movements that can disturb the contents of the plate wells.

PARTS/FEATURES LIST

10 Multi-well plate
100 Overall automatic analysis system
110 Plate hotel
120 Individual plate housing (in hotel)
150 Plate housing shelf (detached)
152 Notch
156 Raised center surface of plate housing shelf
158 rear panel of plate housing
160 Housing shelf
162 Housing shelf hole
164 Connecting rod
166 Housing shelf spacer
200 Gripper
202 Stepper motor (fixed to back support plate 210)
204 Motor mount (fixed to back support plate 210)
206 Coupling (connects stepper motor pin 212 to respective threaded shaft 215)
208 Movable arm mount guide rail (fixed to back support plate 210)
210 Back support plate
212 Stepper motor rotating pins
214 Bearing holder
215 Threaded shaft
220 Laterally movable arm mount
221 Movable arm mount support (moves laterally along rail 208)
222 Threaded lead nut (fixed to respective arm mount 220)
230 Fixed end mount (fixed to back Support plate 210)
240 Fixed intermediate mount (fixed to back support plate 210)
250 Gripper arm (laterally movable)
252 Arm shelf (fixed to respective gripper arm 250)
260 Arm cushion (fixed to respective gripper arm 250)
300 Analysis station
310 Safety platform
320 Microscope/imager
330 Illumination source
410 X-axis guide rails
412 X-axis adjustment motor
420 X-axis adjustment shaft
422 X-axis movable mount
430 Y-axis adjustment shaft
432 Y-axis movable mount
434 Y-axis adjustment motor
440 Vertical support for robot
450 Movable plate stage

DETAILED DESCRIPTION

The inventive gripper and its use in an automated analysis system is shown in the drawings.

Figure 1A:
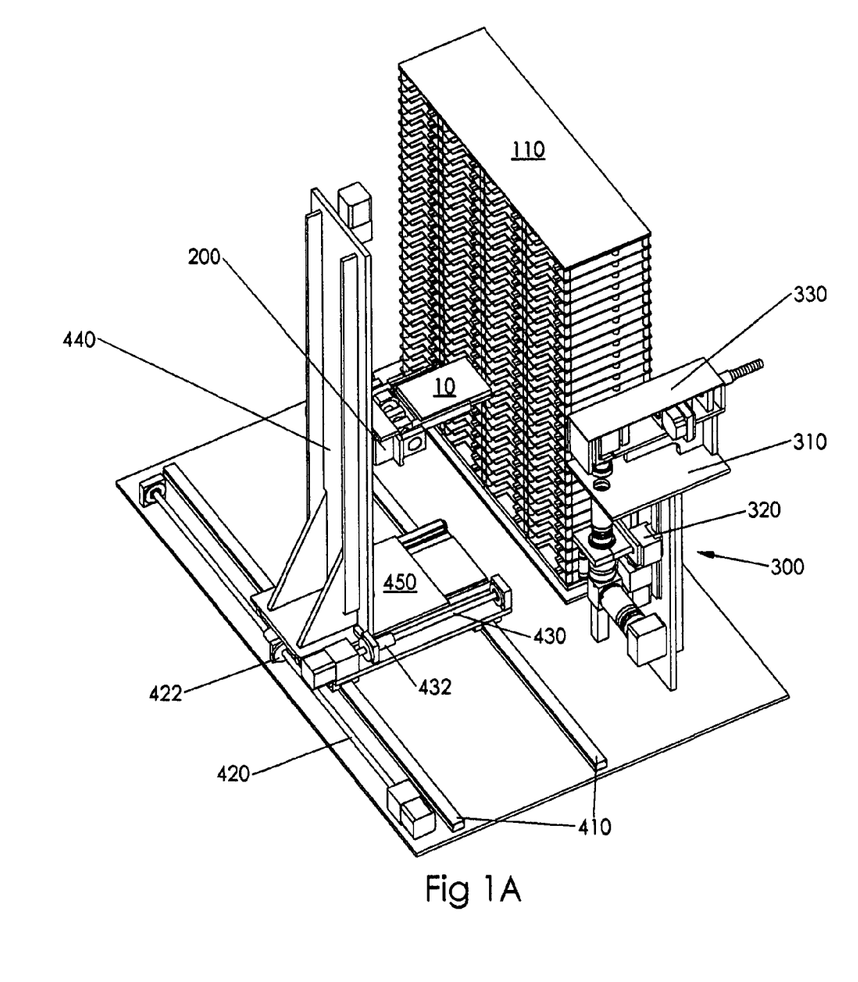
FIGS. 1A, 1B, and 1C show perspective, elevation and plan views of a system using the inventive gripper.

FIG. 1A shows a perspective view of an automated sample analysis system 100 with an X-Y-Z transporting robot. The X-Y-Z robot is computer controlled to move the gripper 200 along three orthogonal directions. A multiwell plate 10 held by the gripper 200 is movable by the robot along a vertical (i.e., Z-axis) support 440. The vertical support 440 is attached to a movable plate stage 450, which is moved along an X-axis on rails 410 by a mount 422 that moves in response to rotation by an X-axis adjustment shaft 420 that, in turn, is controlled by a computer. The plate stage 450 is movable in a Y-axis by movable mount 432 by rotation of Y-axis adjustment shaft 430.

The analysis station 300 includes a safety platform 310 (to prevent a plate from falling below), an imager 320 (such as a microscope and/or CCD camera) and an optional illuminator 330. During analysis, movement of the multiwell plate 10 over the analysis platform 310 is performed by the computer controlled robot, while holding the plate 10 with the gripper 200. The plate is moved incrementally to align successive individual wells in the imaging region, e.g., in the light path between the illuminator 330 and imager 320, thereby imaging each well individually. Upon completion of imaging, the plate 10 is returned by the gripper to its housing shelf in the plate hotel 110.

Alternatively, the plate 10 can be placed by the gripper 200 onto a computer controlled X-Y movable platform instead of the safety platform 310. The X-Y movable platform can perform the necessary incremental movements to align each successive well in the imaging area, such as the light path between the illuminator 330 and the imager 320. In this case, after all wells have been imaged, the plate can be removed with the gripper and returned to the plate hotel 110. Each multiwell plate in the plate hotel that requires analysis is transported to and from the analysis station by the gripper in the same manner.

It is noted that any analytical devices can be used in the analysis stage that permits multiwell plate analysis. In some analytical techniques, the illuminator is not necessary, such as those in which the samples in the wells emit light.

Figure 1B:
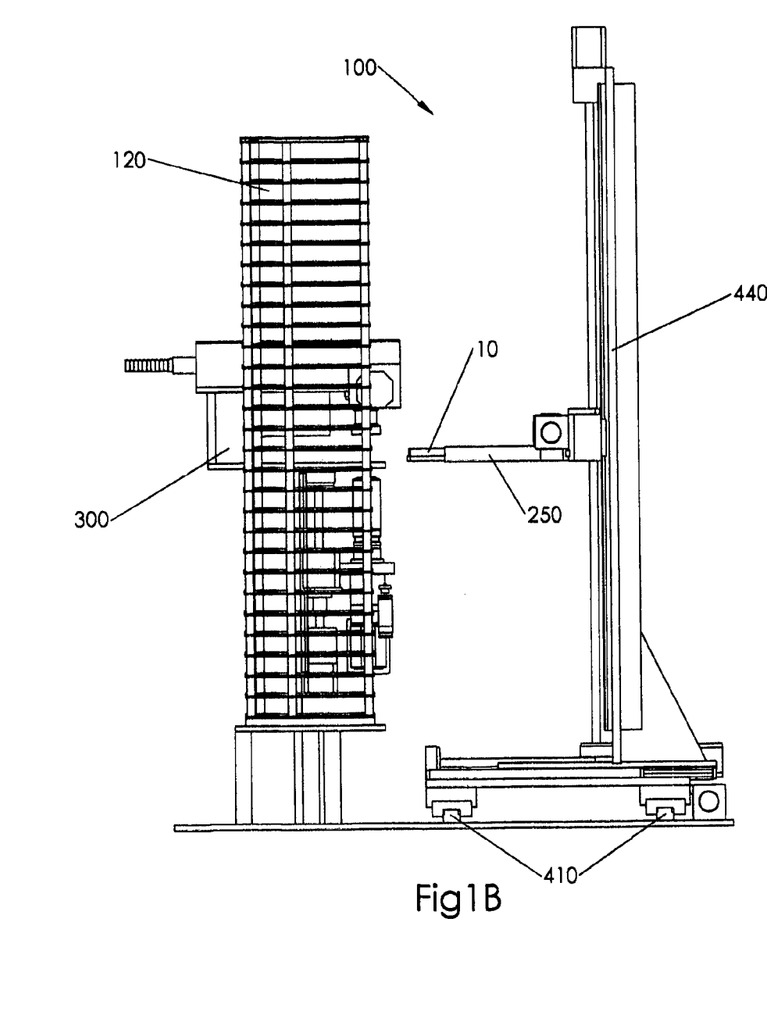

FIG. 1B shows an elevation view of the automated analysis system 100. An individual plate housing 120 is shown assembled with neighboring housings in the plate hotel. The analysis/imaging station 300 is shown behind the plate hotel 110. The Y- and Z-directions are clearly visible in this view.

Figure 1C:
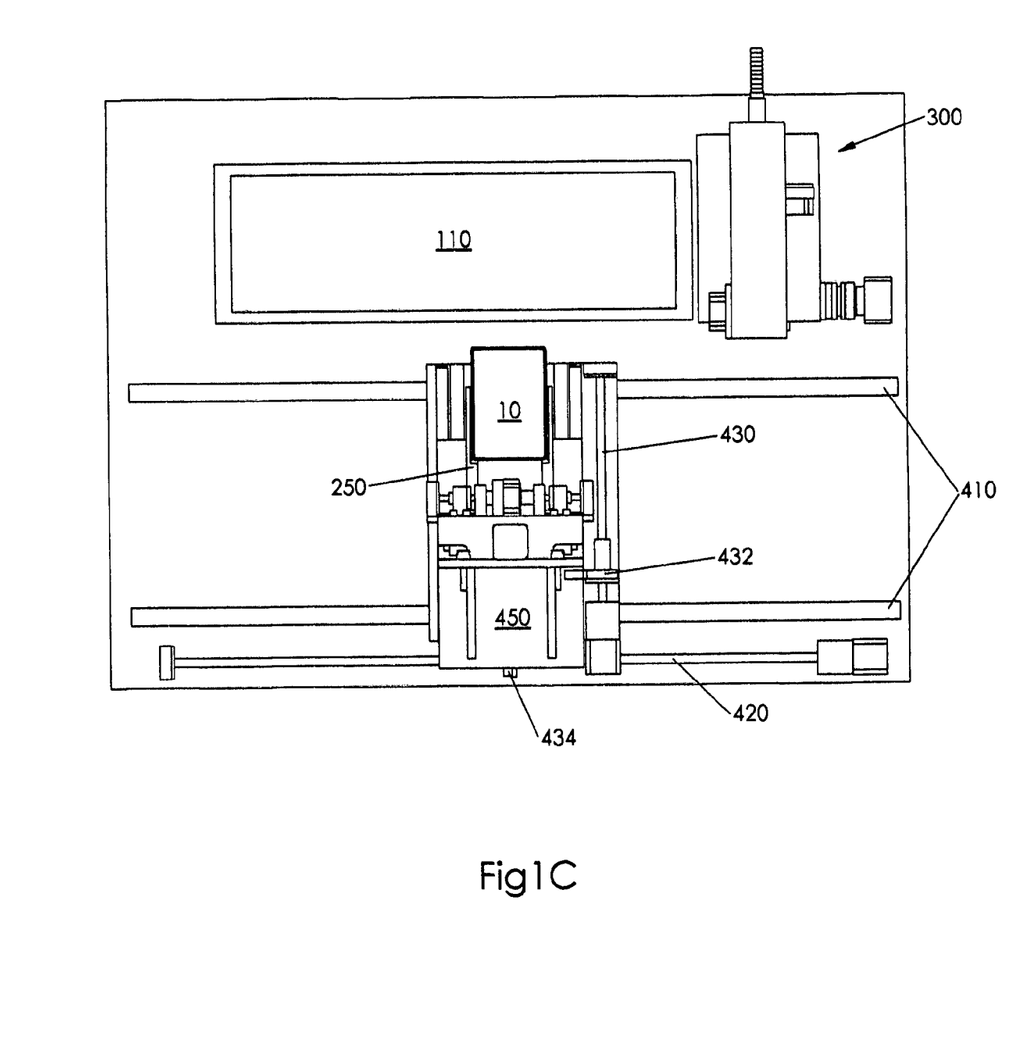

FIG. 1C shows a plan view of the system, including X- and Y-directions and the relative arrangement of the plate hotel 110, the movable plate stage 450 and the analysis stage 300.

Figure 2:
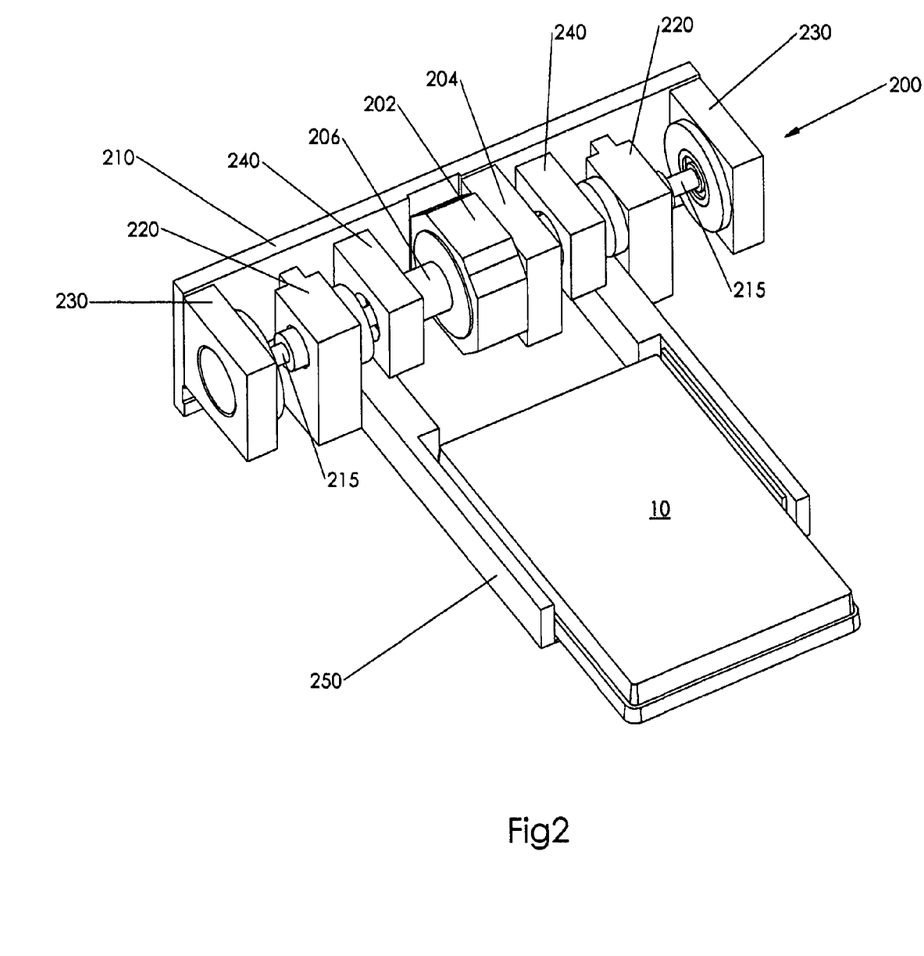
FIG. 2 shows a perspective view of the inventive gripper holding a multi-well plate.
Figure 3A:
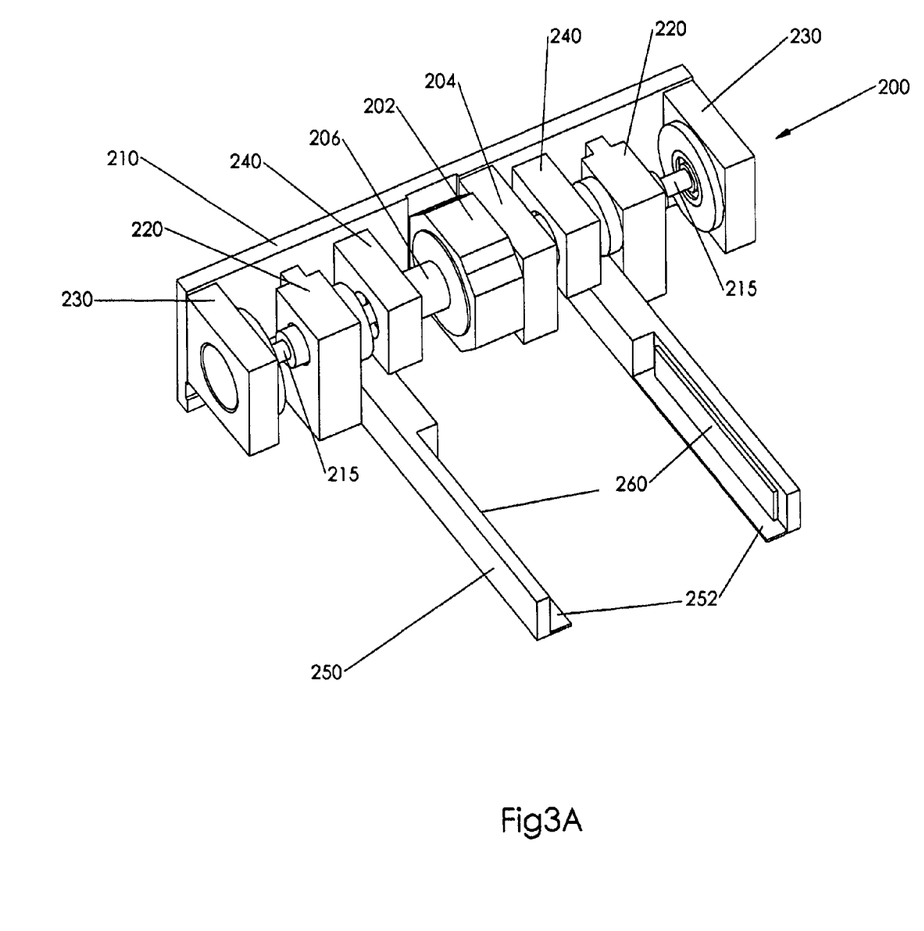
FIGS. 3A, 3B and 3C show perspective, plan and exploded views of the inventive gripper.
Figure 3B:
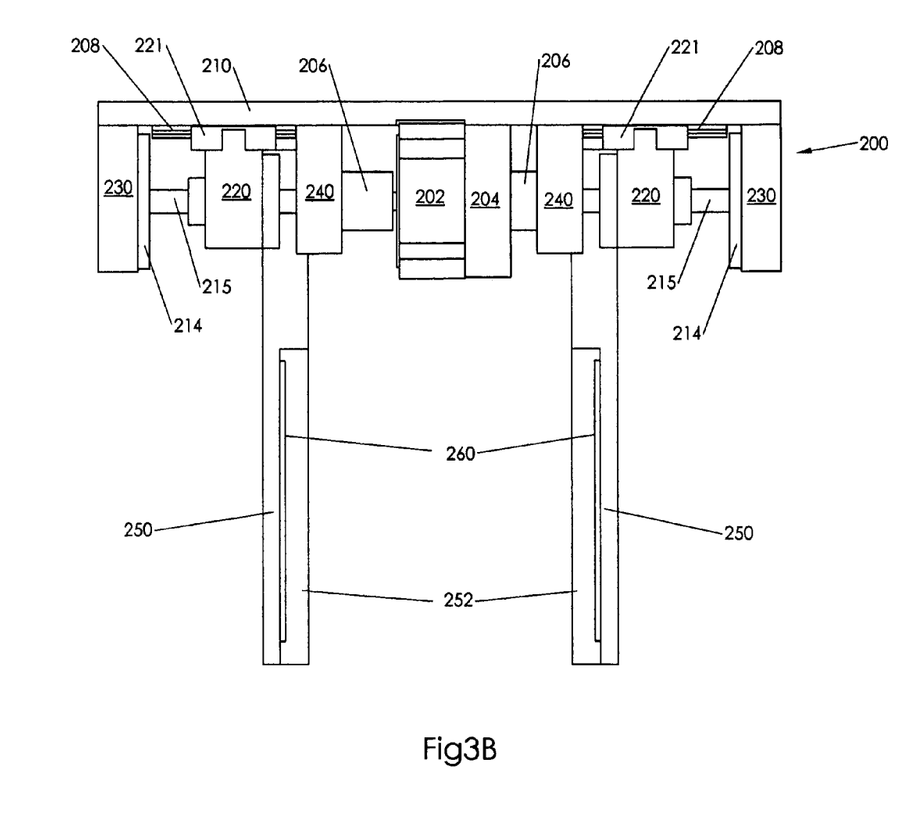
Figure 3C:
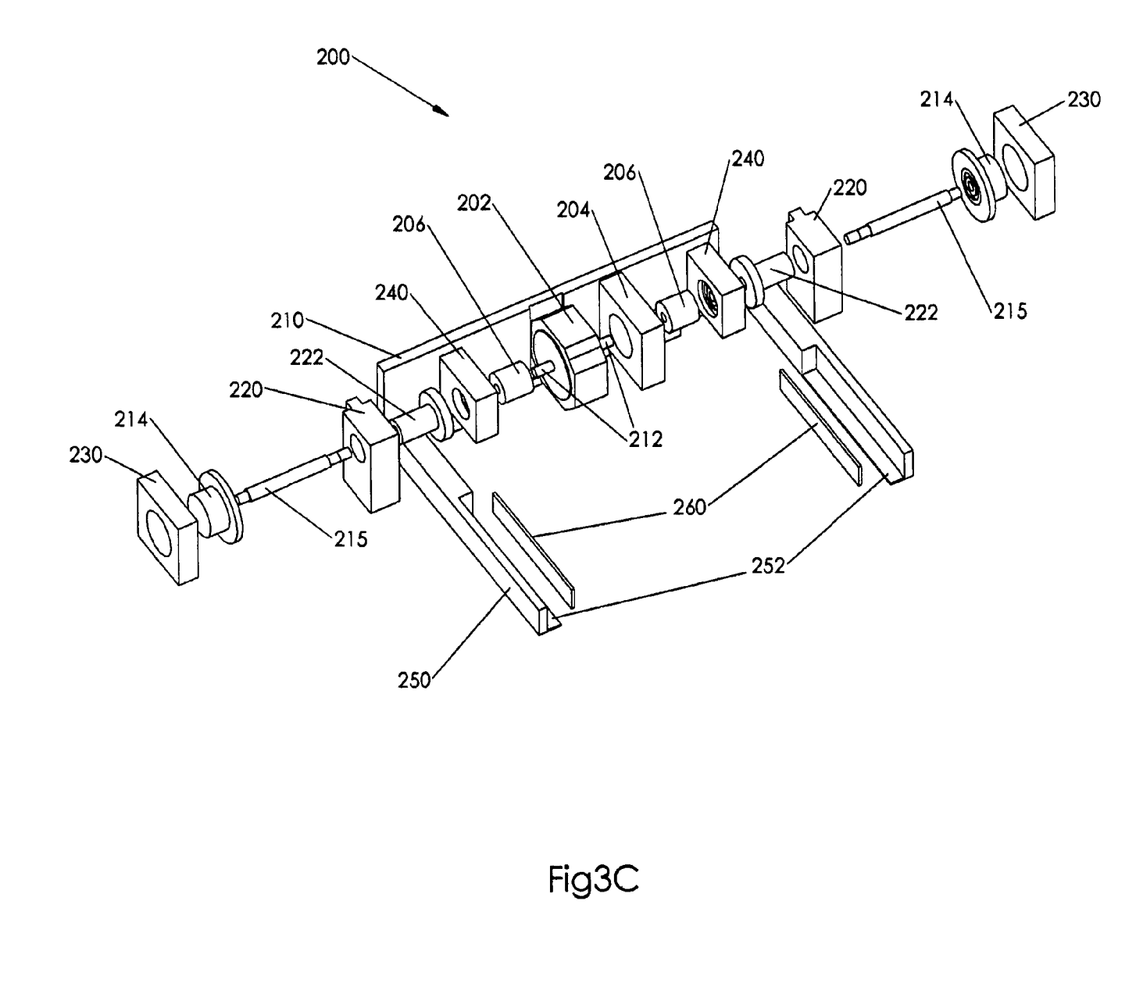

FIG. 2 shows a perspective view of the gripper 200 holding a multiwell plate 10. Also, as shown in FIGS. 3A-C, the pair of gripper arms 250 are movable by rotation of the stepper motor 202 through its respective threaded adjustment shaft 215. When the stepper motor is actuated, it rotates two shafts (215), each shaft having oppositely oriented threads, that cause the mounts 220 to move in simultaneous but opposite linear directions. This causes the pair of arms 250 to move either towards or away from each other, thereby gripping or releasing a multiwell plate, respectively. During rotation of the stepper motor 202, the arm mounts 220 are moved on respective supports 221, FIG. 3B, linearly along a guide rail 208. Intermediate mounts 240 and end mounts 230 acts as holders for bushings or bearings, e.g., 214, for shaft 215. It is noted that stepper motors, per Se, are well known in the art.

More particularly, as shown in FIG. 3C, threaded lead nuts 222, having internal threads that correspond to the threads of the respective shaft 215 on each side of the stepper motor, moves along a linear path by rotation of the shaft 215 by the stepper motor 202. The threaded lead nuts 222 do not rotate during the linear movements. The lead nuts are attached to the respective movable arm mounts 220, that, in turn, move the arms, 250. Movable arms 220 are fixed to respective movable supports 221, that move laterally along rail 208 in response to rotation of the stepper motor, The arm drive mechanism includes all structural elements that enable the arms to grip and release multiwell plates in a controlled manner. The computer, control system and electrical wires that provide communication and power for the various motors in the system are considered known in the art and are not shown.

A cushion 260, such as an adhesively applied resilient foam pad, attached to each of the arms 250 above the respective shelves 252, provides resiliency and a lateral force to hold the multiwell plate securely when the gripper grasps the sides of the multiwell plate 10. The arm shelves 252 ensure that the individual plates are held in a level orientation during transport to the analysis station, and during imaging, thereby ensuring accurate analysis.

Figure 4A:
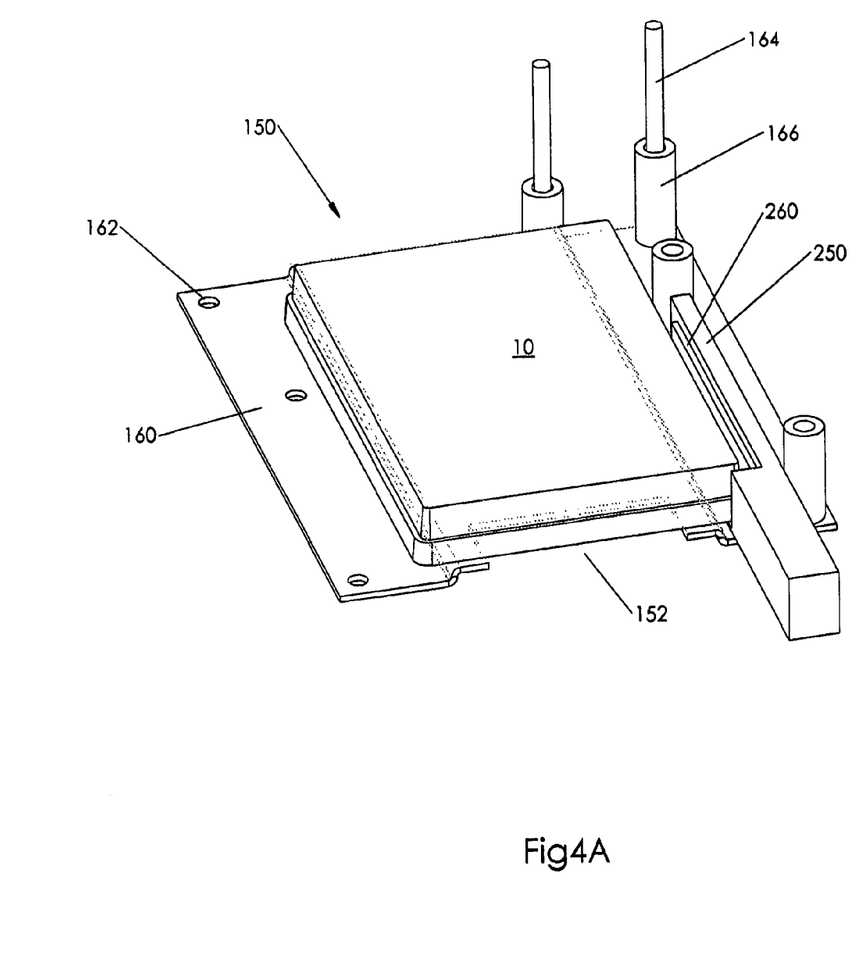
FIGS. 4A, 4B and 4C show a perspective, front and plan view of an individual plate housing.
Figure 4B:
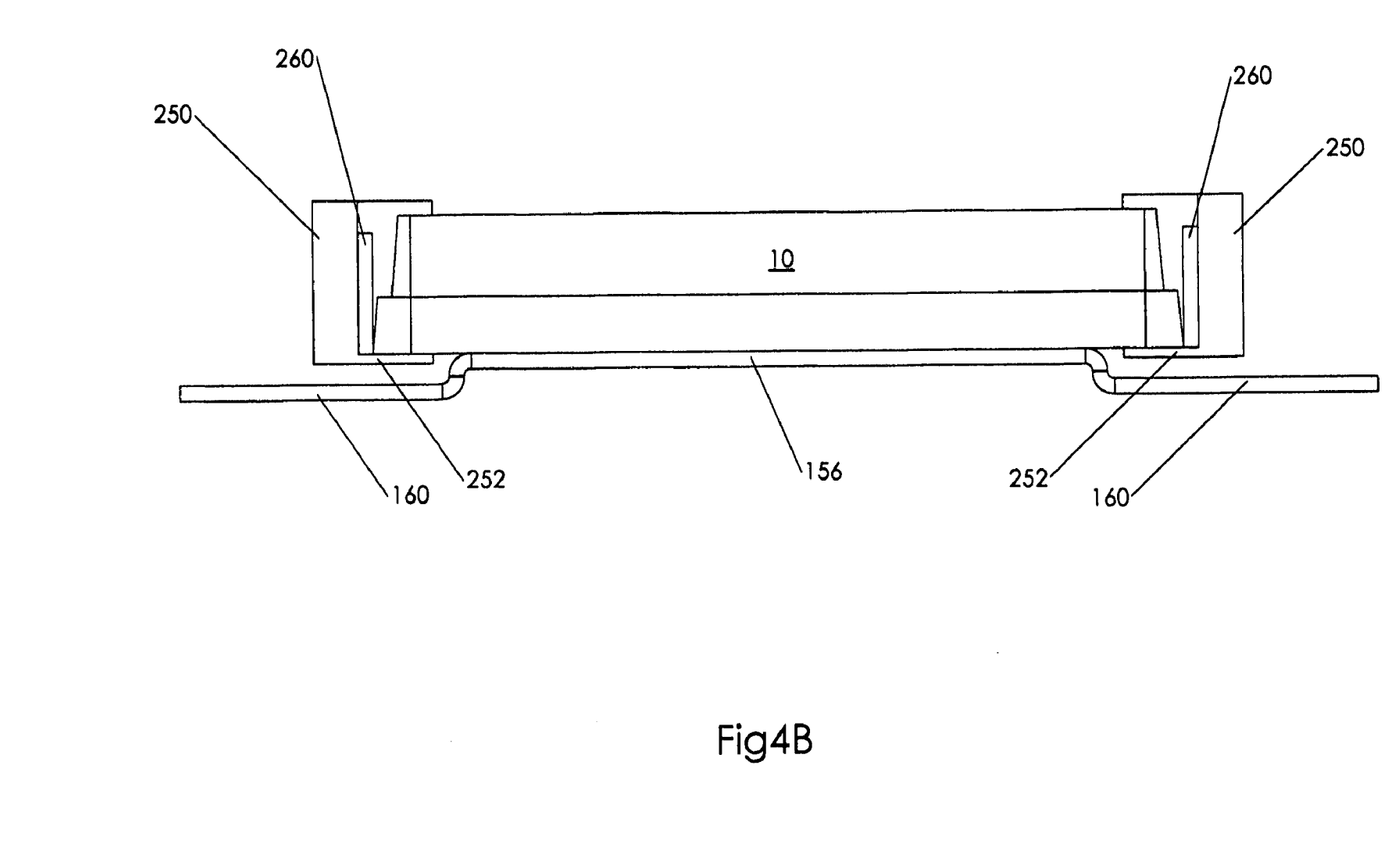
Figure 4C:
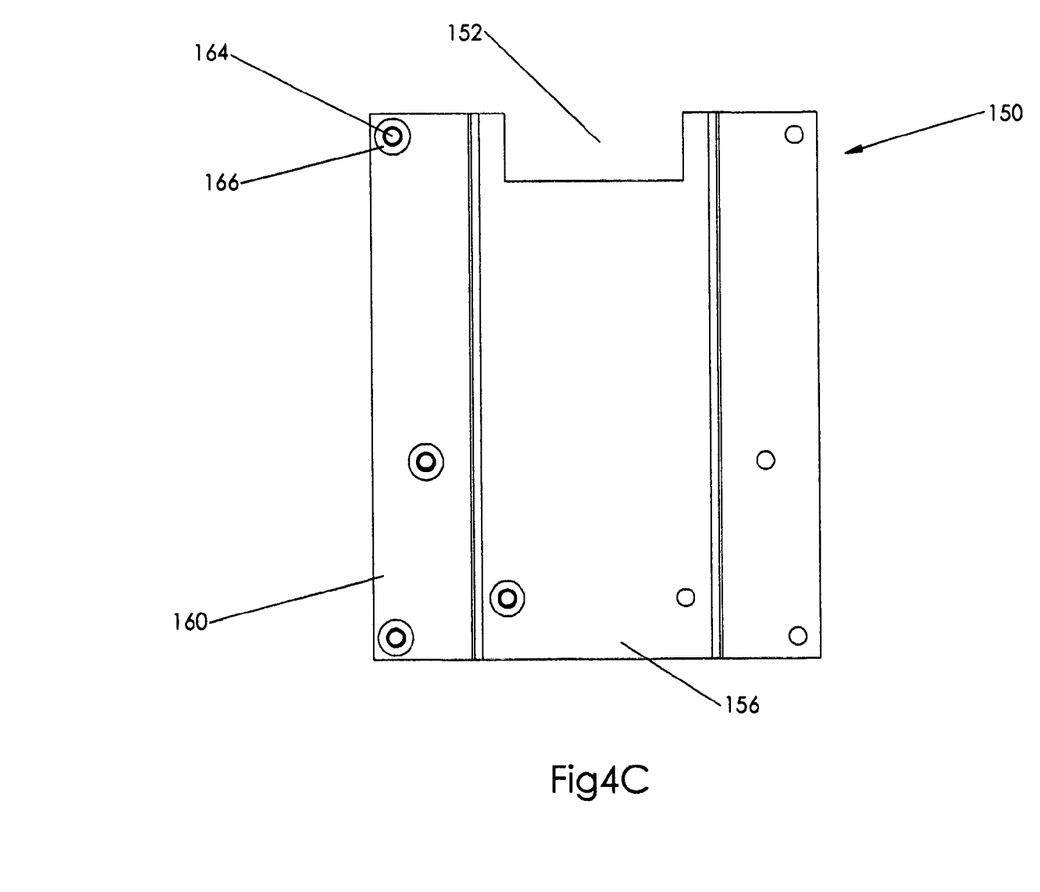

A single housing unit 150 is shown in FIGS. 4A-C in perspective, front elevation and plan views, respectively.

FIGS. 4A and 46 show a multiwell plate 10 resting on a raised portion 156 of a housing shelf 160. Each housing shelf has a front opening through which a multiwell plate can be inserted or removed by the gripper, and a rear panel. Rods 164 pass through holes 162 to connect a stack of housing shelves 160 together, and spacers 166 separate the shelves along the vertical direction.

As shown more particularly in FIG. 4C, the front of the housing shelf 160 has a notch 152 to allow a user to manually insert or remove a plate without tilting the plate. When a plate is contained in the housing 150, it rests on the raised portion 156 of the housing shelf, so that the side edges of the plate extend over the sides of the raised portion 156. When the gripper is extended into the housing to grip a plate (FIG. 4B), the cushions 260 of the gripper arms 250 contact the sides of the plate and the shelves 252 lift the side edges of the plate in a level manner, thereby avoiding unwanted tilting that can adversely affect the contents of the wells.

It is noted that the plate hotel and any or all of its parts can be formed as a molded plastic structure.

The gripper arm components, such as the mounts, supports, arms, bushings, etc. can be machined from aluminum stock, and can be given a protective coating. The attached components can be held together by mechanical means, e.g., screws, and by soldering, welding, and other types of bonding, such as adhesive.

The invention claimed is:

1. An automated analysis system comprising:
    at least one multi-well analysis plate;
    an x-y-z robot having a parallel gripper;
        the parallel gripper composing:
            a support plate configured to maintain a substantially horizontal orientation;
            a stepper motor attached to the support plate, a single pair of opposed threaded shafts extending outwardly from the stepper motor, the two shafts having opposite thread orientation and rotated simultaneously, each threaded shaft being adjustably rotated by the stepper motor;
            a single pair of parallel elongated arms extending from the horizontal support plate, each arm having an upper surface and a lower surface spaced from the upper surface, and each arm having a shelf extending along a portion of the lower surface on the side facing the opposite arm;
            each elongated arm attached to a respective movable mount that moves along the respective shaft in response to rotation of the shafts by the motor, wherein the elongated arms are movable simultaneously by the stepper motor in opposite lateral directions with respect to the support plate to either grip a multi-well plate when the arms are brought together. or to release a multi-well plate when the arms are moved apart, such that each arm shelf provides a horizontal support for the opposing sides of a multi-well plate to maintain the multi-well plate in a level horizontal orientation at all times during gripping and transport;
    a plurality of vertically arranged array of plate housings accessible by the parallel gripper for insertion and removal of individual multi-well plates from the array, each said plate housing comprising:
    an upper surface;
    a lower surface;
    a rear panel connecting the upper and lower surfaces; and
    an opening in the lower surface for inserting and removing a multi-well plate, the lower surface having a notch at the opening to permit the insertion and removal of a multi-well plate, and having a center raised surface to support an inserted multi-well plate, the inserted multi-well plate rests solely on the raised portion to allow the sides of the multi-well plate to be suspended from the side edges of the lower surface, wherein the suspended sides of the inserted multi-well plate correspond to the respective shelves of the elongated gripper arms, wherein the arm shelves of the gripper are configured to be inserted underneath the multi-well plate sides and lift the multi-well plate along its side edges; and a plate analysis station having an optical imager for analyzing the individual wells of the multi-well plate, wherein the parallel gripper is movable by the x-y-z robot to grip and transport the multi-well plate from the plate housing to the plate analysis station and vice versa.

* * * * *